United States Patent
Cui et al.

(10) Patent No.: US 9,551,024 B2
(45) Date of Patent: Jan. 24, 2017

(54) COTTON EVENT PDAB4468.18.07.1 DETECTION METHOD

(71) Applicant: Dow AgroSciences LLC, Indianapolis, IN (US)

(72) Inventors: Yunxing Cory Cui, Carmel, IN (US); Raina King, Indianapolis, IN (US); Tina Marie Kaiser, Carmel, IN (US); Andrew E. Robinson, Brownsburg, IN (US); Dayakar Pareddy, Carmel, IN (US); Sandra Grace Toledo, West Lafayette, IN (US); Leon B. Braxton, Travelers Rest, SC (US); David M. Anderson, Visalia, CA (US)

(73) Assignee: Dow AgroSciences LLC, Indianapolis, IN (US)

( * ) Notice: Subject to any disclaimer, the term of this patent is extended or adjusted under 35 U.S.C. 154(b) by 61 days.

(21) Appl. No.: 13/748,516

(22) Filed: Jan. 23, 2013

(65) Prior Publication Data

US 2013/0189682 A1    Jul. 25, 2013

Related U.S. Application Data

(60) Provisional application No. 61/589,602, filed on Jan. 23, 2012.

(51) Int. Cl.

| | |
|---|---|
| C12Q 1/68 | (2006.01) |
| C12P 19/34 | (2006.01) |
| C12N 15/82 | (2006.01) |
| A01H 1/04 | (2006.01) |

(52) U.S. Cl.
CPC .............. *C12Q 1/6813* (2013.01); *A01H 1/04* (2013.01); *C12N 15/8274* (2013.01); *C12N 15/8277* (2013.01); *C12Q 1/6895* (2013.01); *C12Q 2600/16* (2013.01)

(58) Field of Classification Search
None
See application file for complete search history.

(56) References Cited

U.S. PATENT DOCUMENTS

| | | |
|---|---|---|
| 2010/0281574 A1 | 11/2010 | Zheng et al. |
| 2011/0203017 A1 | 8/2011 | Wright et al. |

OTHER PUBLICATIONS

International Search Report and Written Opinion for PCT/US2013/022727, dated May 14, 2013.
Kumar, et al., "Stable transformation of the cotton plastid genome and maternal inheritance of transgenes," Plant Molecular Biology, Sep. 1, 2004, pp. 203-216, vol. 56, No. 2.
NCBI GenBank Accession No. XM_002514473.1, Aug. 6, 2009.
NCBI GenBank Accession No. EU090199.1, Nov. 7, 2007.
NCBI GenBank Accession No. J01818.1, Dec. 19, 2006.
NCBI GenBank Accession No. AC243160.1, Nov. 13, 2010.

*Primary Examiner* — Young J Kim
(74) *Attorney, Agent, or Firm* — C. Phillip Piorier; Magleby Cataxinos & Greenwood

(57) ABSTRACT

Cotton event pDAB4468.18.07.1 comprises gene expression cassettes which contain genes encoding aad-12 and pat, affording herbicide tolerance to cotton crops containing the event, and enabling methods for crop protection. Embodiments of the subject invention provide polynucleotide-related event detection methods.

4 Claims, 2 Drawing Sheets

Plasmid map of pDAB4468.

The schematic diagram depicts the primer locations for the TaqMan® assay of cotton event pDAB4468.18.07.1.

COTTON EVENT PDAB4468.18.07.1 DETECTION METHOD

CROSS-REFERENCE TO RELATED APPLICATION

This application claims the benefit of the filing date of U.S. Provisional Patent Application Ser. No. 61/589,602, filed Jan. 23, 2012, for "COTTON EVENT pDAB4468.18.07.1 DETECTION METHOD."

BACKGROUND

The gene encoding AAD-12 (aryloxyalkanoate dioxygenase-12) is capable of imparting commercial levels of tolerance to the phenoxyacetic acid herbicides, 2,4-D and MCPA, and the pyridyloxyacetic acid herbicides, triclopyr and fluroxypyr, when expressed in transgenic plants. The gene encoding PAT (phosphinothricin acetyltransferase) is capable of imparting tolerance to the herbicide phoshpinothricin (glufosinate) when expressed in transgenic plants. PAT has been successfully expressed in cotton for use both as a selectable marker, and to impart commercial levels of tolerance to the herbicide glufosinate in transgenic plants.

The expression of transgenes in plants is known to be influenced by their location in the plant genome, perhaps due to chromatin structure (e.g., heterochromatin) or the proximity of transcriptional regulatory elements (e.g., enhancers) close to the integration site (Weising et al., Ann. Rev. Genet 22:421-477, 1988). The presence of the transgene at different locations in the genome will influence the overall phenotype of the plant in different ways. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. As such, it is often necessary to screen a large number of events in order to identify an event characterized by optimal expression of an introduced gene of interest. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It is desirable to be able to detect the presence of a particular event in order to determine whether progeny of a sexual cross contain a transgene or group of transgenes of interest. In addition, a method for detecting a particular event would be helpful for complying with regulations requiring the pre-market approval and labeling of food and fiber derived from recombinant crop plants, for example, or for use in environmental monitoring, monitoring traits in crops in the field, or monitoring products derived from a crop harvest, as well as for use in ensuring compliance of parties subject to regulatory or contractual terms.

It is possible to detect the presence of a transgenic event by any nucleic acid detection method known in the art including, but not limited to, the polymerase chain reaction (PCR) or DNA hybridization using nucleic acid probes. These detection methods generally focus on frequently used genetic elements, such as promoters, terminators, marker genes, etc., because for many DNA constructs, the coding region is interchangeable. As a result, such methods may not be useful for discriminating between different events, particularly those produced using the same DNA construct or very similar constructs unless the DNA sequence of the flanking DNA adjacent to the inserted heterologous DNA is known. For example, an event-specific PCR assay is described in United States Patent Application 2006/0070139 for maize event DAS-59122-7. It would be desirable to have a simple and discriminative method for the identification of cotton event pDAB4468.18.07.1.

DISCLOSURE OF THE INVENTION

Embodiments of the present invention relate to a method for detecting a new insect resistant and herbicide tolerant transgenic cotton transformation event, designated as cotton event pDAB4468.18.07.1, comprising aad-12 and pat as described herein, inserted into a specific site within the genome of a cotton cell. Representative cotton seed has been deposited with the American Type Culture Collection (ATCC), 10801 University Boulevard, Manassas, Va., 20110. The deposit, designated as ATCC Deposit No. PTA-12456, was made on behalf of Dow AgroSciences LLC on Jan. 23, 2012. This deposit was made and will be maintained in accordance with and under the terms of the Budapest Treaty with respect to seed deposits for the purposes of patent procedure.

The DNA of cotton plants containing this event includes the junction/flanking sequences described herein that characterize the location of the inserted DNA within the cotton genome. SEQ ID NO:1 and SEQ ID NO:2 are diagnostic for cotton event pDAB4468.18.07.1. More particularly, sequences surrounding the junctions at bp 2886/2887 of SEQ ID NO:1, and bp147/148 of SEQ ID NO:2 are diagnostic for cotton event pDAB4468.18.07.1. Paragraphs below describe examples of sequences comprising these junctions that are characteristic of DNA of cotton plants containing cotton event pDAB4468.18.07.1.

In one embodiment the invention provides a method of detecting cotton event pDAB4468.18.07.1 in a sample comprising cotton DNA, said method comprising:
(a) contacting said sample with a first primer at least 10 bp in length that selectively binds to a flanking sequence within bp 1-2886 of SEQ ID NO:1 or the complement thereof, and a second primer at least 10 bp in length that selectively binds to an insert sequence within bp 2887-3206 of SEQ ID NO:1 or the complement thereof; and
(b) assaying for an amplicon generated between said primers; or,
(c) contacting said sample with a first primer at least 10 bp in length that selectively binds to an insert sequence within bp 1-147 of SEQ ID NO:2 or the complement thereof, and a second primer at least 10 bp in length that selectively binds to flanking sequence within bp 148-1050 of SEQ ID NO:2 or the complement thereof; and
(d) assaying for an amplicon generated between said primers.

In another embodiment, the invention provides a method of detecting cotton event pDAB4468.18.07.1 comprising:
(a) contacting said sample with a first primer that selectively binds to a flanking sequence selected from the group consisting of bp 1-2886 of SEQ ID NO:1 and bp 148-1050 of SEQ ID NO:2, and compliments thereof; and a second primer that selectively binds to SEQ ID NO:3, or the compliment thereof;

(b) subjecting said sample to polymerase chain reaction; and (c) assaying for an amplicon generated between said primers.

In another embodiment the invention provides an isolated DNA molecule that is diagnostic for cotton event pDAB4468.18.07.1. Such molecules include, in addition to SEQ ID NOS: 1 and 2, molecules at least 40 bp in length comprising bp 1-3206 of SEQ ID NO:1 and at least 40 bp of SEQ ID NO:1 in each direction from the bp 2886/2887 junction; amplicons at least 40 bp in length comprising 1-1050 of SEQ ID NO:2 and at least 40 bp of SEQ ID NO:2 in each direction from the bp 147/148 junction. Examples are bp2867-2906 of SEQ ID NO:1; bp 2837-2936 of SEQ ID NO:1; bp2787-2986 of SEQ ID NO:1; bp2737-3036 of SEQ ID NO:1; bp 128-167 of SEQ ID NO:2; bp 98-197 of SEQ ID NO:2; bp48-247 of SEQ ID NO:2; and bp1-297 of SEQ ID NO:2, and compliments thereof.

Additionally, embodiments of the invention provide assays for detecting the presence of the subject event in a sample (of cotton, for example). The assays can be based on the DNA sequence of the recombinant construct, inserted into the cotton genome, and on the genomic sequences flanking the insertion site. Kits and conditions useful in conducting the assays are also provided.

Embodiments of the invention relate in part to the cloning and analysis of the DNA sequences of the border regions resulting from insertion of T-DNA from pDAB4468 in transgenic cotton lines. These sequences are unique. Based on the insert and junction sequences, event-specific primers can be and were generated. PCR analysis demonstrated that these events can be identified by analysis of the PCR amplicons generated with these event-specific primer sets. Thus, these and other related procedures can be used to uniquely identify cotton lines comprising the event of the subject disclosure.

Brief Description of the Sequences

SEQ ID NO:1 is the 5' DNA flanking border sequence for cotton event pDAB4468.18.07.1. Nucleotides 1-2886 are genomic sequence. Nucleotides 2887-3206 are insert sequence.

SEQ ID NO:2 is the 3' DNA flanking border sequence for cotton event pDAB4468.18.07.1. Nucleotides 1-147 are insert sequence. Nucleotides 148-1050 are genomic sequence.

SEQ ID NO:3 is the T-strand DNA sequence of pDAB4468, which is annotated below in Table 1.

SEQ ID NO:4 is a 132 bp NA fragment that is diagnostic of the 5' integration junction of cotton event pDAB4468.18.07.1.

SEQ ID NO:5 is oligonucleotide primer, ES_1807_F, which was used for the TaqMan® assay to detect the 5' border of cotton event 9582.814.19.1.

SEQ ID NO:6 is oligonucleotide primer, ES_1807_R, which was used for the TaqMan® assay to detect the 5' border of cotton event 9582.814.19.1.

SEQ ID NO:7 is oligonucleotide probe, ES_1807_Pr, which was used for the TaqMan® assay to detect the 5' border of cotton event 9582.814.19.1. This probe had a VIC fluorescent moiety added to the 5' end and an MGB quencher added to the 3' end.

SEQ ID NO:8 is oligonucleotide primer, IC_Sah7F, which was used for the TaqMan® assay to detect the endogenous reference gene, Sah7 (GenBank: AY117065.1).

SEQ ID NO:9 is oligonucleotide primer, IC_Sah7R, which was used for the TaqMan® assay to detect the endogenous reference gene, Sah7 (GenBank: AY117065.1).

SEQ ID NO:10 is oligonucleotide probe, IC_Sah7_Pr, which was used for the TaqMan® assay to detect the endogenous reference gene, Sah7 (GenBank: AY117065.1). This probe had a Cy5fluorescent moiety added to the 5' end and an BHQ2 quencher added to the 3' end.

DETAILED DESCRIPTION

Figure 1:
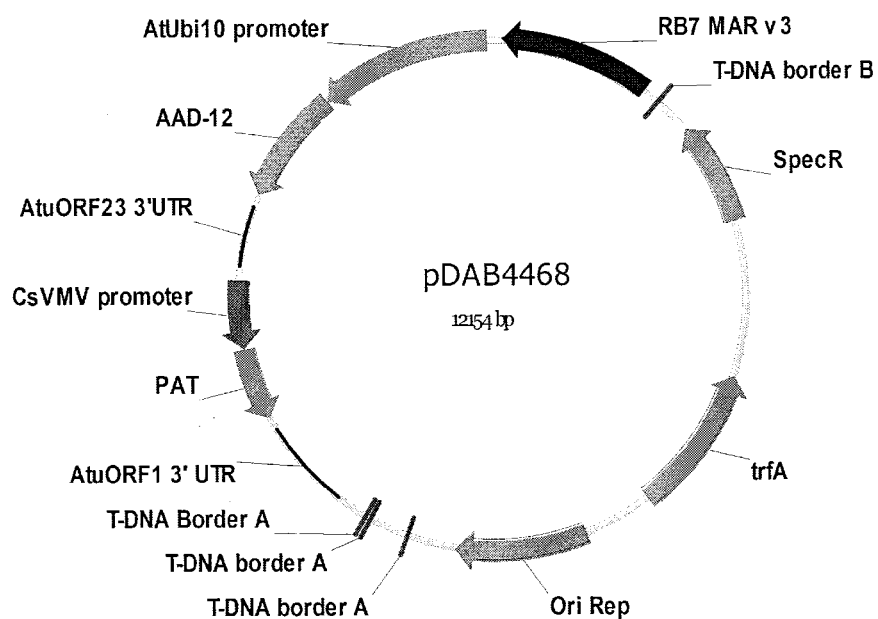
FIG. 1 is a plasmid map of pDAB4468 containing the aad-12 and pat expression cassette.

Both ends of cotton event pDAB4468.18.07.1 insertion have been sequenced and characterized. Event specific assays were developed. The event has also been mapped onto the cotton genome (chromosome 26 of the D genome). The event can be introgressed into further elite lines.

As alluded to above in the Background section, the introduction and integration of a transgene into a plant genome involves some random events (hence the name "event" for a given insertion that is expressed). That is, with many transformation techniques such as Agrobacterium transformation, the biolistic transformation (i.e., gene gun), and silicon carbide mediated transformation (i.e., WHISKERS), it is unpredictable where in the genome a transgene will become inserted. Thus, identifying the flanking plant genomic DNA on both sides of the insert can be important for identifying a plant that has a given insertion event. For example, PCR primers can be designed that generate a PCR amplicon across the junction region of the insert and the host genome. This PCR amplicon can be used to identify a unique or distinct type of insertion event.

Definitions and examples are provided herein to help describe the embodiments of the present invention and to guide those of ordinary skill in the art to practice those embodiments. Unless otherwise noted, terms are to be understood according to conventional usage by those of ordinary skill in the relevant art. The nomenclature for DNA bases as set forth at 37 CFR §1.822 is used.

As used herein, the term "progeny" denotes the offspring of any generation of a parent plant which comprises cotton event pDAB4468.18.07.1.

A transgenic "event" is produced by transformation of plant cells with heterologous DNA, i.e., a nucleic acid construct that includes the transgenes of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA, which would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" or "border sequence" spans the point at which DNA inserted into the genome is linked to DNA from the cotton native genome flanking the insertion point, the identification or detection of one or the other junction sequences in a plant's genetic material being sufficient to be diagnostic for the event. Included are the DNA sequences that span the insertions in herein-described cotton events and similar lengths of flanking DNA. Specific examples of such diagnostic sequences are provided herein; however, other sequences that overlap the junctions of the insertions, or the junctions of the insertions and the genomic sequence, are also diagnostic and could be used in accordance with embodiments of the invention of the subject disclosure.

Embodiments of the invention relate in part to event identification using such flanking, junction, and insert sequences. Related PCR primers and amplicons are included in embodiments of the invention. In accordance with embodiments of the subject invention, PCR analysis methods using amplicons that span across inserted DNA and its borders can be used to detect or identify commercialized transgenic cotton varieties or lines derived from the subject proprietary transgenic cotton lines.

The flanking/junction sequences are diagnostic for cotton event pDAB4468.18.07.1. Based on these sequences, event-specific primers were generated. PCR analysis demonstrated that these cotton lines can be identified in different cotton genotypes by analysis of the PCR amplicons generated with these event-specific primer sets. Thus, these and other related procedures can be used to uniquely identify these cotton lines. The sequences identified herein are unique.

Detection techniques of embodiments of the subject invention are especially useful in conjunction with plant breeding, to determine which progeny plants comprise a given event, after a parent plant comprising an event of interest is crossed with another plant line in an effort to impart one or more additional traits of interest in the progeny. These PCR analysis methods benefit cotton breeding programs as well as quality control, especially for commercialized transgenic cotton seeds. PCR detection kits for these transgenic cotton lines can also now be made and used. This is also beneficial for product registration and product stewardship.

Furthermore, flanking cotton/genomic sequences can be used to specifically identify the genomic location of each insert. This information can be used to make molecular marker systems specific to each event. These can be used for accelerated breeding strategies and to establish linkage data.

Still further, the flanking sequence information can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

In light of all the subject disclosure, it should be clear that embodiments of the subject invention include seeds available under the ATCC Deposit No. PTA-12456. Embodiments of the invention also include a herbicide-tolerant cotton plant grown from a seed deposited with the ATCC Deposit No. PTA-12456. Embodiments of the invention also include parts of said plant, such as leaves, tissue samples, seeds produced by said plant, pollen, and the like (wherein these parts of the plant comprise aad-12, and pat, and SEQ ID NOS: 1 and 2).

As used herein, the term "cotton" means *Gossypium hirsutum* and includes all varieties thereof that can be bred with a cotton plant.

The DNA molecules of embodiments of the invention can be used as molecular markers in a marker assisted breeding (MAB) method. DNA molecules of embodiments of the invention can be used in methods (such as, AFLP markers, RFLP markers, RAPD markers, SNPs, and SSRs) that identify genetically linked agronomically useful traits, as is known in the art. The herbicide-tolerance traits can be tracked in the progeny of a cross with a cotton plant of embodiments of the subject invention (or progeny thereof and any other cotton cultivar or variety) using the MAB methods. The DNA molecules are markers for this trait, and MAB methods that are well known in the art can be used to track the herbicide-tolerant trait(s) in cotton plants where at least one cotton line of embodiments of the subject invention, or progeny thereof, was a parent or ancestor. The methods of embodiments of the invention can be used to identify any cotton variety having the subject event.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, at least three generations.

"Commercial Utility" is defined as having good plant vigor and high fertility, such that the crop can be produced by farmers using conventional farming equipment, and the oil with the described components can be extracted from the seed using conventional crushing and extraction equipment.

"Agronomically elite" means that a line has desirable agronomic characteristics such as yield, maturity, disease resistance, and the like, in addition to the herbicide tolerance due to the subject event(s). Any and all of these agronomic characteristics and data points can be used to identify such plants, either as a point or at either end or both ends of a range of characteristics used to define such plants.

As one skilled in the art will recognize in light of this disclosure, preferred embodiments of detection kits, for example, can include probes and/or primers directed to and/or comprising "junction sequences" or "transition sequences" (where the cotton genomic flanking sequence meets the insert sequence). For example, this includes a polynucleotide probes, primers, and/or amplicons designed to identify one or both junction sequences (where the insert meets the flanking sequence). One common design is to have one primer that hybridizes in the flanking region, and one primer that hybridizes in the insert. Such primers are often each about at least ~15 residues in length. With this arrangement, the primers can be used to generate/amplify a detectable amplicon that indicates the presence of an event of an embodiment of the subject invention. These primers can be used to generate an amplicon that spans (and includes) a junction sequence as indicated above.

The primer(s) "touching down" in the flanking sequence is typically not designed to hybridize beyond about 1200 bases or so beyond the junction. Thus, typical flanking primers would be designed to comprise at least 15 residues of either strand within 1200 bases into the flanking sequences from the beginning of the insert. That is, primers comprising a sequence of an appropriate size from (or hybridizing to) base pairs 1686-3206 of SEQ ID NO:1 and/or base pairs 1-1050 of SEQ ID NO:2 are within the scope of embodiments of the subject invention. Insert primers can likewise be designed anywhere on the insert, but base pairs 1-6368 of SEQ ID NO:3, can be used, for example, non-exclusively for such primer design.

One skilled in the art will also recognize that primers and probes can be designed to hybridize, under a range of standard hybridization and/or PCR conditions wherein the primer or probe is not perfectly complementary to the exemplified sequence. That is, some degree of mismatch or degeneracy can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of an embodiment of the subject invention.

It should be noted that errors in PCR amplification can occur which might result in minor sequencing errors, for example. That is, unless otherwise indicated, the sequences listed herein were determined by generating long amplicons from cotton genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of embodiments of the subject invention.

It should also be noted that it is not uncommon for some genomic sequence to be deleted, for example, when a sequence is inserted during the creation of an event. Thus, some differences can also appear between the subject flanking sequences and genomic sequences listed in GENBANK, for example.

Components of the DNA sequence "insert" are illustrated in the Figures and are discussed in more detail below in the Examples. The DNA polynucleotide sequences of these components, or fragments thereof, can be used as DNA primers or probes in the methods of embodiments of the invention.

In some embodiments of the invention, compositions and methods are provided for detecting the presence of the transgene/genomic insertion region, in plants and seeds and the like, from a cotton plant. DNA sequences are provided that comprise the subject 5' transgene/genomic insertion region junction sequence provided herein (between base pairs 2886/2887 SEQ ID NO:1), segments thereof, and complements of the exemplified sequences and any segments thereof. DNA sequences are provided that comprise the subject 3' transgene/genomic insertion region junction sequence provided herein (between base pairs 147/148 of SEQ ID NO:2), segments thereof, and complements of the exemplified sequences and any segments thereof. The insertion region junction sequence spans the junction between heterologous DNA inserted into the genome and the DNA from the cotton cell flanking the insertion site. Such sequences can be diagnostic for the given event.

Based on these insert and border sequences, event-specific primers can be generated. PCR analysis demonstrated that cotton lines of embodiments of the subject invention can be identified in different cotton genotypes by analysis of the PCR amplicons generated with these event-specific primer sets. These and other related procedures can be used to uniquely identify these cotton lines. Thus, PCR amplicons derived from such primer pairs are unique and can be used to identify these cotton lines.

In some embodiments, DNA sequences that comprise a contiguous fragment of the novel transgene/genomic insertion region are an aspect of embodiments of this invention. Included are DNA sequences that comprise a sufficient length of polynucleotides of transgene insert sequence and a sufficient length of polynucleotides of cotton genomic sequence from one or more of the three aforementioned cotton plants and/or sequences that are useful as primer sequences for the production of an amplicon product diagnostic for one or more of these cotton plants.

Related embodiments pertain to DNA sequences that comprise at least 10, 11, 12, 13, 14, 15, 16, 17, 18, 19, 20, 21, 22, 23, 24, 25, or more contiguous nucleotides of a transgene portion of a DNA sequence identified herein (such as SEQ ID NO:1 and segments thereof), or complements thereof, and a similar length of flanking cotton DNA sequence from these sequences, or complements thereof. Such sequences are useful as DNA primers in DNA amplification methods. The amplicons produced using these primers are diagnostic for any of the cotton events referred to herein. Therefore, embodiments of the invention also include the amplicons produced by such DNA primers.

Embodiments of this invention also include methods of detecting the presence of DNA, in a sample, that corresponds to the cotton event referred to herein. Such methods can comprise: (a) contacting the sample comprising DNA with a primer set that, when used in a nucleic acid amplification reaction with DNA from at least one of these cotton events, produces an amplicon that is diagnostic for said event(s); (b) performing a nucleic acid amplification reaction, thereby producing the amplicon; and (c) detecting the amplicon.

Further detection methods of embodiments of the subject invention include a method of detecting the presence of a DNA, in a sample, corresponding to said event, wherein said method comprises: (a) contacting the sample comprising DNA with a probe that hybridizes under stringent hybridization conditions with DNA from said cotton event and which does not hybridize under the stringent hybridization conditions with a control cotton plant (non-event-of-interest DNA); (b) subjecting the sample and probe to stringent hybridization conditions; and (c) detecting hybridization of the probe to the DNA.

DNA detection kits can be developed using the compositions disclosed herein and methods well known in the art of DNA detection. The kits are useful for identification of the subject cotton event DNA in a sample and can be applied to methods for breeding cotton plants containing this DNA. The kits contain DNA sequences complementary to the amplicons, for example, disclosed herein, or to DNA sequences complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule to which is attached a conventional detectable label or reporter molecule (such as a radioactive isotope, ligand, chemiluminescent agent, or enzyme). Such a probe can hybridize to a strand of a target nucleic acid, in the case of the embodiments of the invention, to a strand of genomic DNA from one of said cotton events, whether from a cotton plant or from a sample that includes DNA from the event. Probes in accordance with embodiments of the invention include not only deoxyribonucleic or ribonucleic acids but also polyamides and other probe materials that bind specifically to a target DNA sequence and can be used to detect the presence of that target DNA sequence.

"Primers" are isolated/synthesized nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of embodiments of the present invention refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, or 1000, or 2000, or 5000 polynucleotides or more in length. Such probes and primers hybridize specifically to a target sequence under stringent hybridization conditions. Preferably, probes and primers in accordance with embodiments of the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of embodiments of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Molecules that exhibit complete complementarity will generally hybridize to one another with sufficient stability to permit them to remain annealed to one another under conventional "high-stringency" conditions. Conventional high-stringency conditions are described by Sambrook et al., 1989.

Two molecules are said to exhibit "minimal complementarity" if they can hybridize to one another with sufficient stability to them to remain annealed to one another under at least conventional "low-stringency" conditions. Conventional low-stringency conditions are described by Sambrook et al., 1989. In order for a nucleic acid molecule to serve as a primer or probe it need only exhibit minimal complementary in sequence to be able to form a stable double-stranded structure under the particular solvent and salt concentrations employed.

The term "stringent condition" or "stringency conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58.

Depending on the application envisioned, one can use varying conditions of stringent conditions or polynucleotide sequence degeneracy of a probe or primer to achieve varying degrees of selectivity of hybridization towards the target sequence. For applications requiring high selectivity, one will typically employ relatively stringent conditions for hybridization of one polynucleotide sequence with a second polynucleotide sequence, e.g., one will select relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well known to those of skill in the art, and the teachings of U.S. Pat. Nos. 4,965,188 and 5,176,995 are exemplary of the methods of hybridization analyses.

A nucleic acid of an embodiment of the present invention will specifically hybridize to one or more of the primers (or amplicons or other sequences) exemplified or suggested herein, including complements and fragments thereof, under high stringency conditions. In one aspect of the present invention, a marker nucleic acid molecule of an embodiment of the present invention has the nucleic acid sequence as set forth herein in one of the exemplified sequences, or complements and/or fragments thereof.

In another aspect of the present invention, a marker nucleic acid molecule of an embodiment of the present invention shares between 80% and 100% or 90% and 100% sequence identity with such nucleic acid sequences. In a further aspect of an embodiment of the present invention, a marker nucleic acid molecule of the present invention shares between 95% and 100% sequence identity with such sequence. Such sequences may be used as markers in plant breeding methods to identify the progeny of genetic crosses. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the cotton plant resulting from a sexual cross contains transgenic event genomic DNA from the cotton plant of an embodiment of the present invention, DNA extracted from a cotton plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. No. 4,683,195 and U.S. Pat. No. 4,683,202. PCR amplification methods have been developed to amplify up to 22 kb of genomic DNA. These methods as well as other methods known in the art of DNA amplification may be used in the practice of embodiments of the present invention. The sequence of the heterologous transgene DNA insert or flanking genomic sequence from a subject cotton event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled ddNTPs specific for the expected next base. Analysis of a bound product can be completed via quantitating the amount of fluorescent signal. A fluorescent signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is designed to hybridize to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension.

Fluorescence Polarization is another method that can be used to detect an amplicon of an embodiment of the present invention. Following this method, an oligonucleotide is designed which overlaps the genomic flanking and inserted DNA junction. The oligonucleotide is hybridized to the single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation of the fluorescently labeled ddNTP can be measured as a change in polarization using a fluorometer. A change in polarization indicates the presence of the transgene insert/flanking sequence due to successful amplification, hybridization, and single base extension.

TaqMan® (PE Applied Biosystems, Foster City, Calif.) is a method of detecting and quantifying the presence of a DNA sequence. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. During specific amplification, the Taq DNA polymerase proofreading mechanism releases the fluorescent moiety away from the quenching moiety on the FRET probe. A fluorescent signal indicates the presence of the flanking/transgene insert sequence due to successful amplification and hybridization.

Molecular Beacons have been described for use in polynucleotide sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

Having disclosed a location in the cotton genome that is excellent for an insertion, embodiments of the subject invention also comprise a cotton seed and/or a cotton plant comprising at least one non-cotton event pDAB4468.18.07.1 insert in the general vicinity of this genomic location. One option is to substitute a different insert in place of the one from cotton event pDAB4468.814.19.1 exemplified herein. In general, targeted homologous recombination, for example, is employed in particular embodiments. This type of technology is the subject of, for example, WO 03/080809 A2 and the corresponding published U.S. application (US 20030232410). Thus, embodiments of the subject invention include plants and plant cells comprising a heterologous insert (in place of or with multi-copies of the aad-12 or pat genes), flanked by all or a recognizable part of the flanking sequences identified herein (bp 1-2886 of SEQ ID NO:1 and bp148-1050 of SEQ ID NO:2). An additional copy (or additional copies) of a aad-12 or pat gene could also be targeted for insertion in this/these manner(s).

The following examples are included to illustrate procedures for practicing embodiments of the invention and to demonstrate certain preferred embodiments of the invention. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention. Unless otherwise indicated, all percentages are by weight and all solvent mixture proportions are by volume unless otherwise noted.

The following abbreviations are used unless otherwise indicated.
bp base pair
° C. degrees Celsius
DNA deoxyribonucleic acid
EDTA ethylenediaminetetraacetic acid
kb kilobase
μg microgram
μL microliter
mL milliliter
M molar mass
PCR polymerase chain reaction
PTU plant transcription unit or expression cassette SDS sodium dodecyl sulfate
SSC a buffer solution containing a mixture of sodium chloride and sodium citrate, pH 7.0
TBE a buffer solution containing a mixture of Tris base, boric acid and EDTA, pH 8.3

EXAMPLES

Example 1

Transformation and Selection of the Aad-12 and Pat Cotton Event pDAB4468.18.07.1

Transgenic cotton (*Gossypium hirsutum*) containing the cotton event pDAB4468.18.07.1 was generated through Agrobacterium-mediated transformation and selected using medium containing glufosinate. The disarmed Agrobacterium strain EHA101 (Hood et al., 1993), carrying the binary vector pDAB4468 (FIG. 1) containing gene expression cassettes comprised of the selectable marker, pat, and the gene of interest, aad-12, within the T-strand DNA region was used to initiate transformation of cotton variety Coker 310. The DNA T-strand sequence for pDAB4468 is given in SEQ ID NO:3, which is annotated below in Table 1.

TABLE 1

Gene elements located on pDAB4468.

| bp (SEQ ID NO: 3) | Construct element | Reference |
| --- | --- | --- |
| 139-1,304 bp | RB7 MAR v3 | Thompson et al., 1997; WO9727207 |
| 1,400-2,721 bp | AtUbi10 Promoter | Callis, et al., (1990) J. Biol. Chem., 265: 12486-12493 |
| 2,730-3,611 bp | AAD-12 | WO 2007/053482 |
| 3,714-4,170 bp | ORF23 3'UTR | U.S. Pat. No. 5,428,147 |
| 4,285-4,801 bp | CsVMV Promoter | Verdaguer et al., (1996) Plant Mol. Biol., 31: 1129-1139 |
| 4,809-5,360 bp | PAT | Wohlleben et al., (1988) Gene 70: 25-37 |
| 5,463-6,166 bp | ORF1 3'UTR | Huang et al., (1990) J. Bacteriol. 172: 1814-1822 |

Example 2

Event Specific TaqMan® Assay

Figure 2:
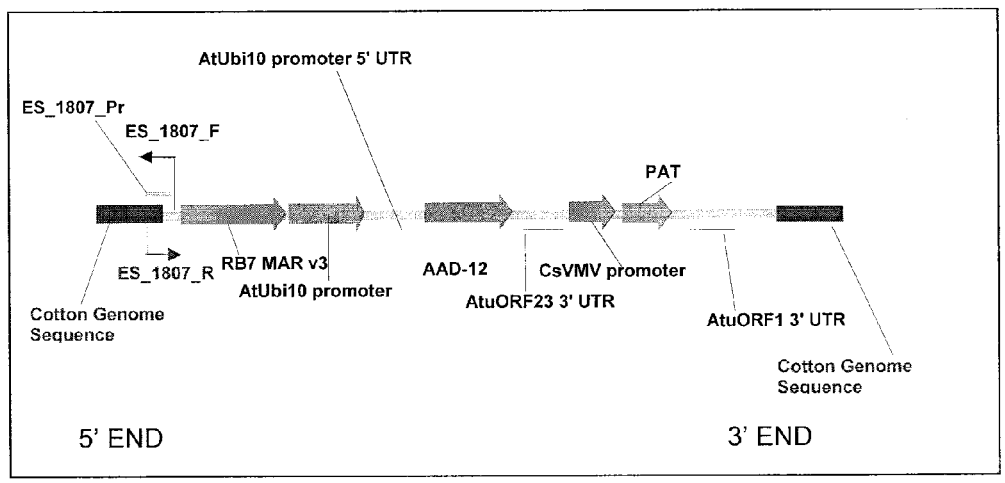
FIG. 2 depicts the primer and probe locations for the TaqMan® assay of the cotton event pDAB4468.18.07.1.

An event specific TaqMan® assay was developed to detect the presence of cotton event pDAB4468.18.07.1. Cotton event pDAB4468.18.07.1 contains the T-strand of the binary vector pDAB4468 (FIG. 1). For detection of cotton event pDAB4468.18.07.1, specific TaqMan® primers and probe were designed according to the DNA sequences located in the 5' (SEQ ID NO:1) insert-to-plant junction (FIG. 2). The event specific assay for cotton event pDAB4468.18.07.1 was designed to specifically detect a 132 bp DNA fragment (SEQ ID NO:4) that spans the 5' integration junction using two primers and a target-specific MGB probe synthesized by Applied Biosystems (ABI) containing the VIC reporter at its 5'end. Specificity of this TaqMan® detection method for cotton event pDAB4468.18.07.1 was tested against cotton event pDAB4468.18.07.1 and the non-transgenic near-isoline control cotton variety, Coker 310, in duplex format. The amplification results of cotton event pDAB4468.18.07.1 were normalized using the cotton specific endogenous reference gene, Sah7 (GenBank Accession No: AY117065.1).

Example 3 gDNA Isolation

Genomic DNA (gDNA) samples were isolated from the cotton event pDAB4468.18.07.1 and non-transgenic cotton control line, Coker 310. Genomic DNA was extracted using a modified 96-Well Qiagen Dneasy plant DNA Kit™ (Qiagen, Valencia, Calif.). Fresh cotton cotyledon leaf discs, 6 per sample, were used for gDNA extraction. The gDNA was quantified with the PicoGreen™ method according to vendor's instructions (Molecular Probes, Eugene, Oreg.). Samples were diluted by a 1/5 dilution with DNase-free® water.

Example 4

TaqMan® Assay and Results

Specific TaqMan® primers and probes were designed for the cotton event pDAB4468.18.07.1 specific assay. These reagents can be used with the conditions listed below to detect the presence of the closely linked aad-12 and pat gene expression cassettes within cotton event pDAB4468.18.07.1. Table 2 lists the primer and probe sequences that were developed specifically for the detection of cotton event pDAB4468.18.07.1.

TABLE 2

PCR Primers and Probes

| Name | Description | 5' to 3' Sequence |
| --- | --- | --- |
| Event Target Reaction | | |
| (SEQ ID NO: 5) ES_1807_F | Event specific forward primer | GCTTTCTAATTTCAAACTATTCGG |
| (SEQ ID NO: 6) ES_1807_R | Event specific reverse primer | AAACTTAAATGGCATGTTGCAA |
| (SEQ ID NO: 7) ES_1807_Pr | Event specific probe used | Vic-TTTGTCTATGCACCACCC-MGB |
| Reference Gene Reaction | | |
| (SEQ ID NO: 8) IC_Sah7F | Reference forward primer | AGTTTGTAGGTTTTGATGTTACATTGAG |

TABLE 2-continued

PCR Primers and Probes

| Name | Description | 5' to 3' Sequence |
|---|---|---|
| (SEQ ID NO: 9) IC_Sah7R | Reference reverse primer | GCATCTTTGAACCGCCTACTG |
| (SEQ ID NO 10) IC_Sah7_Pr | Reference probe | Cy5-AAACATAAAATAATGGGAACAACCATGACATGT-BHQ2 |

The multiplex PCR conditions for amplification were: 1× Roche PCR Buffer, 0.4 µM event specific forward primer, 0.4 µM event specific reverse primer, 0.4 µM primer IC_Sah7F, 0.4 µM primer IC_Sah7R, 0.2 µM event specific probe, 0.2 µM IC_Sah7 Pr probe, 0.1% PVP, 2 µL of 5× diluted gDNA in a total reaction of 10 µl. The cocktail was amplified using the following conditions: i) 95° C. for 10 min., ii) 95° C. for 10 sec, iii) 55° C. for 40 sec, repeat step ii-iii for 40 cycles, iv) 40° C. hold. The TaqMan® PCR was carried out on the Roche LightCycler 480®. Data analysis, which indicated the presence of cotton event pDAB4468.18.07.1, was based on measurement of the crossing point (Cp value) determined by LightCycler 480® software, which is the PCR cycle number when the rate of change in fluorescence reaches its maximum level of amplification.

The TaqMan® detection method was developed to test and detect cotton event pDAB4468.18.07.1 which contains the aad-12 and pat gene expression cassettes and to normalize the levels of expression using the cotton specific, endogenous reference gene Sah7 (GenBank: AY117065.1). The assay specifically detected the cotton event pDAB4468.18.07.1 and did not produce or amplify any false-positive results from the control (i.e., the non-transgenic cotton variety Coker310). Moreover, the developed assay can be used in a multiplex format which contains gDNA samples from non-transgenic plants, and/or other transgenic events. Disclosed for the first time is a polynucleotide detection method that can be used to specifically identify cotton event pDAB4468.18.07.1 in samples. The event specific primers and probe can be used for the detection of cotton event pDAB4468.18.07.1 in samples and these conditions and reagents are applicable for zygosity assays.

Having illustrated and described the principles of the present invention, it should be apparent to persons skilled in the art that the invention can be modified in arrangement and detail without departing from such principles. We claim all modifications that are within the spirit and scope of the appended claims.

What is claimed is:

1. A method of detecting cotton event pDAB4468.18.07.1 in a sample comprising cotton DNA, said method comprising:

contacting said sample with a first primer at least 10 bp in length that selectively binds to a flanking sequence within by 1-2886 of SEQ ID NO:1 or the complement thereof, and a second primer at least 10 bp in length that selectively binds to an insert sequence within by 2887-3206 of SEQ ID NO:1 or the complement thereof; and assaying for an amplicon generated between said primers, wherein the amplicon consists of a polynucleotide comprised within SEQ ID NO:1.

2. The method according to claim 1, wherein said sample comprising cotton DNA is obtained from cotton plants comprising event pDAB4468.18.07.1 that have been deposited under ATCC accession number PTA-12456.

3. The method according to claim 1, wherein the first primer comprises the polynucleotide of SEQ ID NO:5, and wherein the second primer comprises the polynucleotide of SEQ ID NO:6.

4. The method of claim 3, wherein said sample comprising cotton DNA is obtained from cotton plants comprising event pDAB4468.18.07.1 that have been deposited under ATCC accession number PTA-12456.

* * * * *

SEQUENCE LISTING

```
<160> NUMBER OF SEQ ID NOS: 10

<210> SEQ ID NO 1
<211> LENGTH: 3206
<212> TYPE: DNA
<213> ORGANISM: Artificial Sequence
<220> FEATURE:
<223> OTHER INFORMATION: 5' DNA flanking border sequence for cotton
      event pDAB4468.18.07.1

<400> SEQUENCE: 1
ccatggttcc aacaaatgag tacaaatttg catttgggtc ctcacattta acaatagctt      60
taaagtcccg aaagttatag tcattatgta aggatgaagt tacctctagt gcttgtttga     120
gtttcaaatt tgtttctcca tcaaggttca tggtctcaac ataacagact gcatcctcgt     180
aactggatgc aagcaagatg aggtctgttg gaaagaattc atctttctcc acctttacaa     240
tatctcccac tctaagattc ttccattcag tatgatgaaa gttgccatca ccttgatgaa     300
cttttacctt tctgttgttc acctctatat cctgaagaaa ttccagattg aacaagaaat     360
tttagaacaa agaaaacaac caggttatgg aaactttacg tataagctaa ttttgcagtt     420
ctaagatgca tctggctcaa tctaacgagc agcaagatag tagtgtaaag aaagttcaat     480
gtctatggca ccaacgaaga ccaatattta aggtagacag agaattgagt tacacatagc     540
ttagttaaaa caactcgata taccaaaagg aaaaattaaa agtgaaagat agatgtattt     600
tatggcaatc aagaaggcct agagatccag aaaaaggaag aagctattga agaatatgtt     660
ctgatccttt ttaaaggcct aaatgcactt ggcacaatta tattaggcaa atggaagcac     720
ttacaatcat gtaaactatt taagaagccc tttctataaa tgactatata ttttatggac     780
```

```
tccataaagg gaaagatgat agagaaagta aaaaataagg agtgcaaagg gaagcaacta      840
tctggcacct taagtagcaa ctaaaaagaa atgaagcagc agcagcagca aagcgaaaag      900
aaagaaggta ataaagtaaa taaagaaggg agtgaaacct gctgttgtcg gcgccaatcc      960
tcaacacctt ctttgatcat agtagcgcca ataacgatga tgagagggac gatagcacta     1020
agagcggaat aaggagcaat agcagtgaag gaaagaatac cagtgaccaa aaagaagaag     1080
ttggcgaccc tcctgaattg ctcgaacaag gacttgggca agaatgtagc aacggtatac     1140
ttggtagtac tgacataatt atcagagtaa ttacgggttc ccgcctccaa ggaatttggt     1200
tcattacaat aaacaatcct ggaaaatccc ggccccccaa tctgggagtg gtcttccttg     1260
aatgatgctt taccacatgc aaccccatag atcctgctca tcaacacctt tctcctccta     1320
ccaccactca ttttccttgt ttctctcttt agctacaaat taattaatta actttatgca     1380
gctttaattt cttcaccccc ccccactaa tatgtgcccc tttgatctta atttcaccct      1440
aacagtgtat gtacggtatg tttgtacata tgcattcaac tataagaaga agaagaaaat     1500
ttatataaaa taaagcagag gatcccagtt tacaaaaaaa aaaaaaaaag accaacgcag     1560
ataaagcctg ggttgttgct gtttaactca aagtcccaga aaatgaacaa atacaagaaa     1620
taaataatag aatattttcc ccaggcagaa agtgaataaa ggtttagact ttaaggagag     1680
agagagagag aggaagaaga agaagaagaa gaaatagata gctttggaca aaggaaaaca     1740
ctacattaaa gatacaaata tataaggata tatatatatg tatgtaagca tgtaagattt     1800
agtcttgaaa agagaaagtg ttgagaaaca gggtgaaggg agaatatata aatttaaaac     1860
ggttttgttt aatcaagata ttaggaagat ggcgctgtta ttgaggtcat caactgaaaa     1920
cacacaaaaa cgaagaagcg aagaaaaata ttggaagttg aaagttcaga tgatactaca     1980
tgaataaatt ttcttcagat gatactacat gaataaattt tctttcctcg ttttatttct     2040
gtatcttcag ctgaagcttt gatttgaacg gtgactttga ttttgatgac tttctttttt     2100
tctttttttc tttttttttt tttatgtgtt ctatgtacgc gcattttgat tttcccttt      2160 ggaggccaag acaaaagaaa attaatacta gctccaaata taaaattcaa acttttgta     2220 tattttgtgc atatggatat ttaatttacg tctaattctt ctttcaatcc ctctactctt     2280
ttcatattta aattttagtc tctctacttt tggtctttga aatttattcc ttaatttaat     2340
aattacgatc caattaaata atattgtcaa accacttcta ataaattgaa ttatgtagta     2400
tttttaaaat aaaagtttgc tcacagtgac taacattaca tggaaaacta aaaatgttaa     2460
atataatgtt gtaacgaatt taaaattata agattttca atactatttg agagaagtaa     2520
gatgaaagtc gatttttttt cttatttaca tgattttctt tctatcaaag ttttaataa      2580 ttggatttca ataattaaat ataatgaatt ttttaataa aacattaaat gttattacta      2640
attgctagag gcatcgatta ttacaacatc gtgaattaca tcaataagaa agaaaaatga     2700
ataaactaga aaaaaaaatc tagtaaaaat atccggacac aaaaaatatt aacaaagaaa     2760
gagaaatgat gtataaagca ggattttta cctaagtaat attaaaaaaa aacttaaatg      2820
gcatgttgca aaaattatgt actaaaatag tacgttcaaa tgggtggagg gtggtgcata     2880
gacaaaccag tcagcatcat cacaccaaaa gttaggcccg aatagtttga aattagaaag     2940
ctcgcaattg aggtctacag gccaaattcg ctcttagccg tacaatatta ctcaccggat     3000
cctaaccggt gtgatcatgg gccgcgatta aaatctcaa ttatatttgg tctaatttag      3060
tttggtattg agtaaaacaa attcgaacca aaccaaaata taaatatata gtttttatat     3120
```

```
atatgcctttt aagactttt  atagaatttt  ctttaaaaaa tatctagaaa tatttgcgac      3180
tcttctggca tgtaatattt cgttaa                                              3206

<210> SEQ ID NO 2
<211> LENGTH: 1050
<212> TYPE: DNA
<213> ORGANISM: Artificial Sequence
<220> FEATURE:
<223> OTHER INFORMATION: 3' DNA flanking border sequence for cotton
      event pDAB4468.18.07.1

<400> SEQUENCE: 2
gcacatagac acacacatca tctcattgat gcttggtaat aattgtcatt agattgtttt         60
tatgcataga tgcactcgaa atcagccaat tttagacaag tatcaaacgg atgtgacttc        120
agtacattaa aaacgtccgc aatgtgtagt gtctatctga taggcggcac tggtggtgcc        180
tatctgatag acgacacacc tagtattccc cccccacact cccccatcca gctcatttta        240
aatatttatt aaaacaccta aattttatat gttgttttta attataaaaa aaataccaaa        300
cagttttgtc cacatcatat ttttgctat  actacactaa caaaataaat atatcttata        360
aattccaact taaactccaa cttaatggtc tcattcacaa atttcatctc aatggtttaa        420
tcttttacct acataaaaaa acaaaaaaat tatattaaaa taataaaaat aacatgccaa        480
taaaaaatat aacaaaaata taacataaat gatacataat aaatacgaat attattatta        540
ttttaaaatg ataataagta aaatgttttg gtttaaaata taatatatat aaaacatgcc        600
aacttaatta ttgtcaaaaa atatcatttt tttgcataca acttcaaaag aaatcttatt        660 ttaatatttta taaaaaacat aaaatataaaat ttaaaaacat aaactcttat tctcaataaa    720
ctcttattct caattataaa atcttaaaaa attagaacat ataaactaat tcctaattta        780
tctaataaat tacaaattcc atatcaatgg tctcatcttt tacctacata aaaaaataaa        840
aataaaaata ttaaaataat taaaataaca tgccaaataa attttataaa aaaataaatc        900 taatcaaacct aaaacacaca taacaaataa attacataaa aaataaaaata ttttttgtac     960 ataacataaa taggtttttt ttacttcaat aaatattaaa aataaattat gaatgaatga       1020 aaatatataaa taaatacaaa catacattag                                        1050

<210> SEQ ID NO 3
<211> LENGTH: 6368
<212> TYPE: DNA
<213> ORGANISM: Artificial Sequence
<220> FEATURE:
<223> OTHER INFORMATION: T-strand DNA sequence of pDAB4468

<400> SEQUENCE: 3
ccagtcagca tcatcacacc aaaagttagg cccgaatagt ttgaaattag aaagctcgca         60
attgaggtct acaggccaaa ttcgctctta gccgtacaat attactcacc ggatcctaac        120
cggtgtgatc atgggccgcg attaaaaatc tcaattatat ttggtctaat ttagtttggt        180
attgagtaaa acaaattcga accaaaccaa aatataaata tatagttttt atatatatgc        240
ctttaagact ttttatagaa ttttctttaa aaaatatcta gaaatatttg cgactcttct        300
ggcatgtaat atttcgttaa atatgaagtg ctccattttt attaacttta aataattggt        360
tgtacgatca ctttcttatc aagtgttact aaaatgcgtc aatctctttg ttcttccata        420
ttcatatgtc aaaacctatc aaaattctta tatatctttt tcgaatttga agtgaaattt        480
cgataattta aaattaaata gaacatatca ttatttaggt atcatattga ttttatact         540
```

```
taattactaa atttggttaa cttttgaaagt gtacatcaac gaaaaattag tcaaacgact    600
aaaataaata aatatcatgt gttattaaga aaattctcct ataagaatat tttaatagat    660
catatgtttg taaaaaaaat taatttttac taacacatat atttacttat caaaaatttg    720
acaaagtaag attaaaataa tattcatcta acaaaaaaaa aaccagaaaa tgctgaaaac    780
ccggcaaaac cgaaccaatc caaaccgata tagttggttt ggtttgattt tgatataaac    840
cgaaccaact cggtccattt gcacccctaa tcataatagc tttaatattt caagatatta    900
ttaagttaac gttgtcaata tcctggaaat tttgcaaaat gaatcaagcc tatatggctg    960
taatatgaat ttaaaagcag ctcgatgtgg tggtaatatg taatttactt gattctaaaa   1020
aaatatccca agtattaata atttctgcta ggaagaaggt tagctacgat ttacagcaaa   1080
gccagaatac aatgaaccat aaagtgattg aagctcgaaa tatacgaagg aacaaatatt   1140
tttaaaaaaa tacgcaatga cttggaacaa agaaagtga tatattttt gttcttaaac   1200
aagcatcccc tctaaagaat ggcagttttc ctttgcatgt aactattatg ctcccttcgt   1260
tacaaaaatt ttggactact attgggaact tcttctgaaa atagtggcca ccgcttaatt   1320
aaggcgcgcc atgcccgggc aagcggccgc acaagtttgt acaaaaaagc aggctccgcg   1380
gtgactgact gaaaagcttg tcgacctgca ggtcaacgga tcaggatatt cttgtttaag   1440
atgttgaact ctatggaggt ttgtatgaac tgatgatcta ggaccggata agttcccttc   1500
ttcatagcga acttattcaa agaatgtttt gtgtatcatt cttgttacat tgttattaat   1560
gaaaaaatat tattggtcat tggactgaac acgagtgtta aatatggacc aggccccaaa   1620
taagatccat tgatatatga attaaataac aagaataaat cgagtcacca aaccacttgc   1680
cttttttaac gagacttgtt caccaacttg atacaaaagt cattatccta tgcaaatcaa   1740
taatcataca aaaatatcca ataacactaa aaaattaaaa gaatggata atttcacaat   1800
atgttatacg ataaagaagt tacttttcca agaaattcac tgatttata gcccacttg   1860
cattagataa atggcaaaaa aaaacaaaaa ggaaaagaaa taaagcacga agaattctag   1920
aaaatacgaa atacgcttca atgcagtggg acccacggtt caattattgc caattttcag   1980
ctccaccgta tatttaaaaa ataaaacgat aatgctaaaa aaatataaat cgtaacgatc   2040
gttaaatctc aacggctgga tcttatgacg accgttagaa attgtggttg tcgacgagtc   2100
agtaataaac ggcgtcaaag tggttgcagc cggcacacac gagtcgtgtt tatcaactca   2160
aagcacaaat acttttcctc aacctaaaaa taaggcaatt agccaaaaac aactttgcgt   2220
gtaaacaacg ctcaatacac gtgtcatttt attattagct attgcttcac cgccttagct   2280
ttctcgtgac ctagtcgtcc tcgtcttttc ttcttcttct tctataaaac aatacccaaa   2340
gcttcttctt cacaattcag atttcaattt ctcaaaatct taaaactttt ctctcaattc   2400
tctctaccgt gatcaaggta aatttctgtg ttccttattc tctcaaaatc ttcgattttg   2460
ttttcgttcg atcccaattt cgtatatgtt ctttggttta gattctgtta atcttagatc   2520
gaagacgatt ttctgggttt gatcgttaga tatcatctta attctcgatt agggtttcat   2580
aaatatcatc cgatttgttc aaataattg agttttgtcg aataattact cttcgatttg   2640
tgatttctat ctagatctgg tgttagtttc tagtttgtgc gatcgaattt gtcgattaat   2700
ctgagttttt ctgattaaca gagatctcca tggctcagac cactctccaa atcacaccca   2760
ctggtgccac cttgggtgcc acagtcactg gtgttcacct tgccacactt gacgatgctg   2820
gtttcgctgc cctccatgca gcctggcttc aacatgcact cttgatcttc cctgggcaac   2880
acctcagcaa tgaccaacag attacctttg ctaaacgctt tggagcaatt gagaggattg   2940
```

```
gcggaggtga cattgttgcc atatccaatg tcaaggcaga tggcacagtg cgccagcact    3000
ctcctgctga gtgggatgac atgatgaagg tcattgtggg caacatggcc tggcacgccg    3060
actcaaccta catgccagtc atggctcaag gagctgtgtt cagcgcagaa gttgtcccag    3120
cagttggggg cagaacctgc tttgctgaca tgagggcagc ctacgatgcc cttgatgagg    3180
caacccgtgc tcttgttcac caaaggtctg ctcgtcactc ccttgtgtat tctcagagca    3240
agttgggaca tgtccaacag gccgggtcag cctacatagg ttatggcatg gacaccactg    3300
caactcctct cagaccattg gtcaaggtgc atcctgagac tggaaggccc agcctcttga    3360
tcggccgcca tgcccatgcc atccctggca tggatgcagc tgaatcagag cgcttccttg    3420
aaggacttgt tgactgggcc tgccaggctc ccagagtcca tgctcaccaa tgggctgctg    3480
gagatgtggt tgtgtgggac aaccgctgtt tgctccaccg tgctgagccc tgggatttca    3540
agttgccacg tgtgatgtgg cactccagac tcgctggacg cccagaaact gagggtgctg    3600
ccttggtttg agtagttagc ttaatcacct agagctcggt caccagcata attttattta    3660
atgtactaaa ttactgtttt gttaaatgca atttgctttt tcgggatttt aatatcaaa    3720 atctatttag aaatacacaa tattttgttg caggcttgct ggagaatcga tctgctatca    3780
taaaaattac aaaaaaattt tatttgcctc aattatttta ggattggtat taaggacgct    3840
taaattattt gtcgggtcac tacgcatcat tgtgattgag aagatcagcg atacgaaata    3900
ttcgtagtac tatcgataat ttatttgaaa attcataaga aaagcaaacg ttacatgaat    3960
tgatgaaaca atacaaagac agataaagcc acgcacattt aggatattgg ccgagattac    4020
tgaatattga gtaagatcac ggaatttctg acaggagcat gtcttcaatt cagcccaaat    4080
ggcagttgaa atactcaaac cgccccatat gcaggagcgg atcattcatt gtttgtttgg    4140
ttgcctttgc caacatggga gtccaaggtt gcggccgcgc gccgaccag ctttcttgta    4200 caaagtggtt gcggccgctt aattaaattt aaatgcccgg gcgtttaaac gcggccgctt    4260
aattaaggcc ggcctgcagc aaacccagaa ggtaattatc caagatgtag catcaagaat    4320
ccaatgttta cgggaaaaac tatggaagta ttatgtaagc tcagcaagaa gcagatcaat    4380
atgcggcaca tatgcaacct atgttcaaaa atgaagaatg tacagataca agatcctata    4440
ctgccagaat acgaagaaga atacgtagaa attgaaaaag aagaaccagg cgaagaaaag    4500
aatcttgaag acgtaagcac tgacgacaac aatgaaaaga agaagataag gtcggtgatt    4560
gtgaaagaga catagaggac acatgtaagg tggaaaatgt aagggcggaa agtaacctta    4620
tcacaaagga atcttatccc ccactactta tccttttata ttttttccgtg tcattttgc    4680 ccttgagttt tcctatataa ggaaccaagt tcggcatttg tgaaaacaag aaaaaatttg    4740
gtgtaagcta ttttctttga agtactgagg atacaacttc agagaaattt gtaagtttgt    4800
agatctccat gtctccggag aggagaccag ttgagattag gccagctaca gcagctgata    4860 tggccgcgt ttgtgatatc gttaaccatt acattgagac gtctacagtg aactttagga    4920
cagagccaca acaccacaa gagtggattg atgatctaga gaggttgcaa gatagatacc    4980
cttggttggt tgctgaggtt gagggtgttg tggctggtat tgcttacgct gggccctgga    5040
aggctaggaa cgcttacgat tggacagttg agagtactgt ttacgtgtca cataggcatc    5100
aaaggttggg cctaggatcc acattgtaca cacatttgct taagtctatg gaggcgcaag    5160
gttttaagtc tgtggttgct gttataggcc ttccaaacga tccatctgtt aggttgcatg    5220
aggctttggg atacacagcc cggggtacat tgcgcgcagc tggatacaag catggtggat    5280
ggcatgatgt tggttttgg caaagggatt ttgagttgcc agctcctcca aggccagtta    5340
```

```
ggccagttac ccagatctga ggtaccctga gcttgagctt atgagcttat gagcttagag   5400
ctcggatcca ctagtaacgg ccgccagtgt gctggaattc gcccttgact agataggcgc   5460
ccagatcggc ggcaatagct tcttagcgcc atcccgggtt gatcctatct gtgttgaaat   5520
agttgcggtg ggcaaggctc tctttcagaa agacaggcgg ccaaaggaac ccaaggtgag   5580
gtgggctatg gctctcagtt ccttgtggaa gcgcttggtc taaggtgcag aggtgttagc   5640
gggatgaagc aaaagtgtcc gattgtaaca agatatgttg atcctacgta aggatattaa   5700
agtatgtatt catcactaat ataatcagtg tattccaata tgtactacga tttccaatgt   5760
ctttattgtc gccgtatgta atcggcgtca caaataatc cccggtgact ttcttttaat    5820
ccaggatgaa ataatatgtt attataattt ttgcgatttg gtccgttata ggaattgaag   5880
tgtgcttgcg gtcgccacca ctcccatttc ataatttac atgtatttga aaataaaaa    5940 tttatggtat tcaatttaaa cacgtatact tgtaaagaat gatatcttga aagaaatata   6000
gtttaaatat ttattgataa aataacaagt caggtattat agtccaagca aaaacataaa   6060
tttattgatg caagtttaaa ttcagaaata tttcaataac tgattatatc agctggtaca   6120
ttgccgtaga tgaaagactg agtgcgatat tatggtgtaa tacatagcgg ccgggttct    6180 agtcaccggt taggatccgt ttaaactcga ggctagcgca tgcacataga cacacacatc   6240
atctcattga tgcttggtaa taattgtcat tagattgttt ttatgcatag atgcactcga   6300
aatcagccaa ttttagacaa gtatcaaacg gatgtgactt cagtacatta aaaacgtccg   6360
caatgtgt                                                           6368

<210> SEQ ID NO 4
<211> LENGTH: 132
<212> TYPE: DNA
<213> ORGANISM: Artificial Sequence
<220> FEATURE:
<223> OTHER INFORMATION: 5' integration junction of cotton event
      pDAB4468.18.07.1

<400> SEQUENCE: 4
gctttctaat ttcaaactat tcgggcctaa cttttggtgt gatgatgctg actggtttgt    60
ctatgcacca ccctccaccc atttgaacgt actattttag tacataattt ttgcaacatg   120
ccatttaagt tt                                                       132

<210> SEQ ID NO 5
<211> LENGTH: 24
<212> TYPE: DNA
<213> ORGANISM: Artificial Sequence
<220> FEATURE:
<223> OTHER INFORMATION: oligonucleotide primer, ES_1807_F

<400> SEQUENCE: 5
gctttctaat ttcaaactat tcgg                                           24

<210> SEQ ID NO 6
<211> LENGTH: 22
<212> TYPE: DNA
<213> ORGANISM: Artificial Sequence
<220> FEATURE:
<223> OTHER INFORMATION: oligonucleotide primer, ES_1807_R

<400> SEQUENCE: 6
aaacttaaat ggcatgttgc aa                                             22
```

```
<210> SEQ ID NO 7
<211> LENGTH: 18
<212> TYPE: DNA
<213> ORGANISM: Artificial Sequence
<220> FEATURE:
<223> OTHER INFORMATION: oligonucleotide probe, ES_1807_Pr

<400> SEQUENCE: 7
tttgtctatg caccaccc                                                 18

<210> SEQ ID NO 8
<211> LENGTH: 28
<212> TYPE: DNA
<213> ORGANISM: Artificial Sequence
<220> FEATURE:
<223> OTHER INFORMATION: oligonucleotide primer, IC_Sah7F

<400> SEQUENCE: 8
agtttgtagg ttttgatgtt acattgag                                      28

<210> SEQ ID NO 9
<211> LENGTH: 21
<212> TYPE: DNA
<213> ORGANISM: Artificial Sequence
<220> FEATURE:
<223> OTHER INFORMATION: oligonucleotide primer, IC_Sah7R

<400> SEQUENCE: 9
gcatctttga accgcctact g                                             21

<210> SEQ ID NO 10
<211> LENGTH: 33
<212> TYPE: DNA
<213> ORGANISM: Artificial Sequence
<220> FEATURE:
<223> OTHER INFORMATION: oligonucleotide probe, IC_Sah7_Pr

<400> SEQUENCE: 10
aaacataaaa taatgggaac aaccatgaca tgt                                33
```